US00PP37522P2

(12) United States Plant Patent
Mathey

(10) Patent No.: US PP37,522 P2
(45) Date of Patent: Jul. 14, 2026

(54) ***DIERVILLA* PLANT NAMED 'SMNDSA'**

(50) Latin Name: ***Diervilla* x *splendens***
Varietal Denomination: SMNDSA

(71) Applicant: Megan M. Mathey, Holland, MI (US)

(72) Inventor: Megan M. Mathey, Holland, MI (US)

(73) Assignee: SPRING MEADOW NURSERY, INC., Grand Haven, MI (US)

( * ) Notice: Subject to any disclaimer, the term of this patent is extended or adjusted under 35 U.S.C. 154(b) by 0 days.

(21) Appl. No.: 19/383,647

(22) Filed: Nov. 8, 2025

(51) Int. Cl.
*A01H 5/02* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./226
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Diervilla* plant named 'SMNDSA', characterized by its compact, upright to outwardly spreading and uniformly mounding plant habit; vigorous growth habit and rapid growth rate; freely branching habit; dense and bushy appearance; dark green-colored leaves; numerous greenish yellow-colored flowers that produce dark red-colored fruits; and good garden performance.

4 Drawing Sheets

Figure 1:
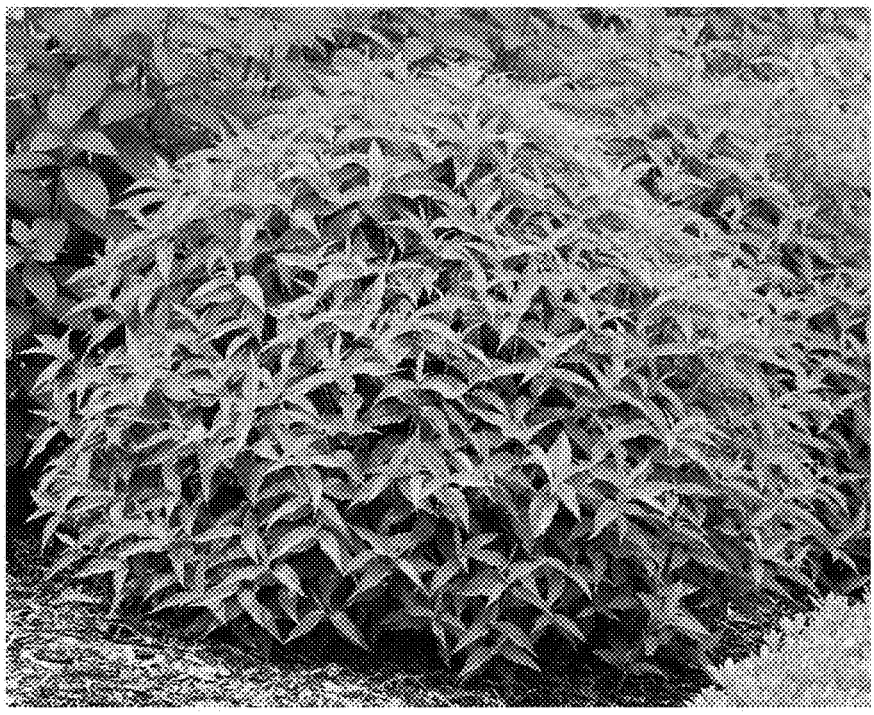

Botanical designation: *Diervilla* x *splendens.*
Cultivar denomination: 'SMNDSA'.

BACKGROUND OF THE INVENTION

The present invention relates to a new and distinct cultivar of *Diervilla* plant, botanically known as *Diervilla* x *splendens*, commonly referred to as a hybrid Bush Honeysuckle and hereinafter referred to by the cultivar name 'SMNDSA'.

The new *Diervilla* is a product of a planned breeding program conducted by the Inventor in Grand Haven, Michigan. The objective of the breeding program was to develop new compact and freely branching *Diervilla* plants with unique leaf shape and color.

The new *Diervilla* plant originated from an open-pollination during the summer of 2020 in Grand Haven, Michigan of *Diervilla* x *splendens* 'Beauregard', not patented, as the female, or seed, parent with an unknown proprietary selection of *Diervilla* x *splendens* as the male, or pollen, parent. The new *Diervilla* plant was discovered and selected by the Inventor during the summer of 2022 as a single flowering plant within the progeny of the stated cross-pollination in a controlled environment in Grand Haven, Michigan.

Asexual reproduction of the new *Diervilla* plant by softwood stem cuttings in a controlled greenhouse environment in Grand Haven, Michigan since the summer of 2022 has shown that the unique features of this new *Diervilla* plant are stable and reproduced true to type in successive generations of asexual reproduction.

SUMMARY OF THE INVENTION

Plants of the new *Diervilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNDSA'. These characteristics in combination distinguish 'SMNDSA' as a new and distinct *Diervilla* plant:

1. Compact, upright to outwardly spreading and uniformly mounding plant habit.
2. Vigorous growth habit and rapid growth rate.
3. Freely branching habit; dense and bushy appearance.
4. Dark green-colored leaves.
5. Numerous greenish yellow-colored flowers that produce dark red-colored fruits.
6. Good garden performance.

Plants of the new *Diervilla* can be compared to plants of the female parent, 'Beauregard'. In side-by-side comparisons, plants of the new *Diervilla* differ primarily from plants of 'Beauregard' in the following characteristics:

1. Plants of the new *Diervilla* are more freely and uniformly branching and denser than plants of 'Beauregard'.
2. Leaves of the new *Diervilla* are flatter than and not as concave as leaves of plants of 'Beauregard'.
3. Plants of the new *Diervilla* produce more fruits than plants of 'Beauregard'.

Plants of the new *Diervilla* can be compared to plants of *Diervilla sessifolia* 'Butterfly', not patented. In side-by-side comparisons, plants of the new *Diervilla* differ primarily from plants of 'Butterfly' in the following characteristics:

1. Plants of the new *Diervilla* are more freely and uniformly branching and denser than plants of 'Butterfly'.
2. Plants of the new *Diervilla* produce more fruits than plants of 'Butterfly'.

BRIEF DESCRIPTION OF THE PHOTOGRAPHS

The accompanying colored photographs illustrate the overall appearance of the new *Diervilla* plant showing the colors as true as it is reasonably possible to obtain in colored reproductions of this type. Colors in the photographs may differ slightly from the color values cited in the detailed botanical description which accurately describe the colors of the new *Diervilla* plant.

The photograph on the first sheet (FIG. 1) is a side perspective view of a typical vegetative plant of 'SMNDSA'.

Figure 2:
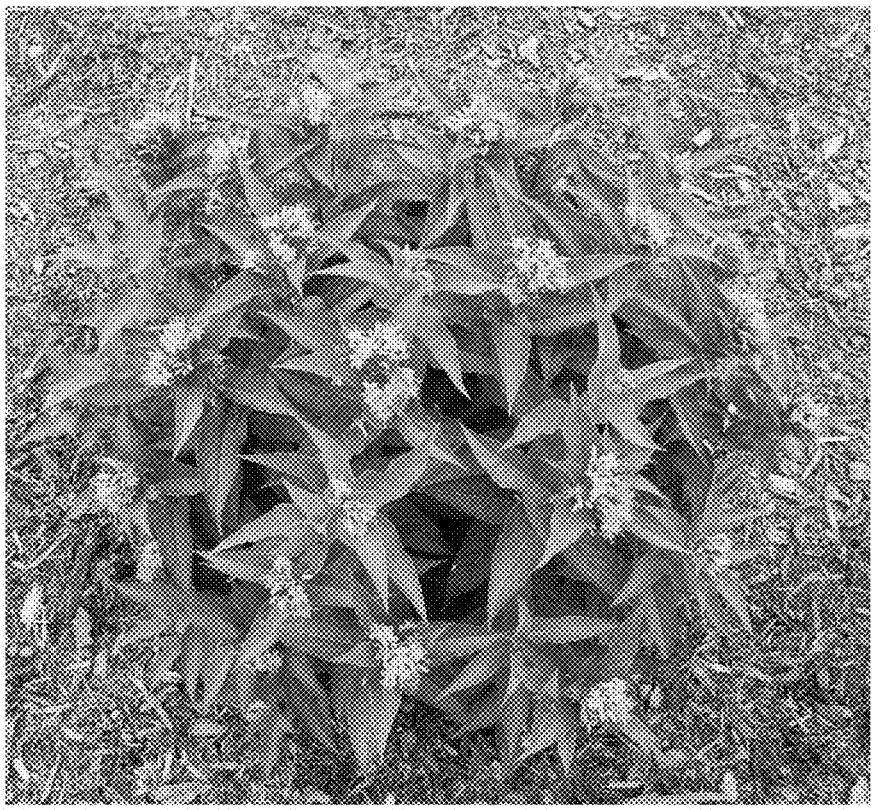

The photograph on the second sheet (FIG. 2) is a overhead view of a typical flowering plant of 'SMNDSA'.

Figure 3:
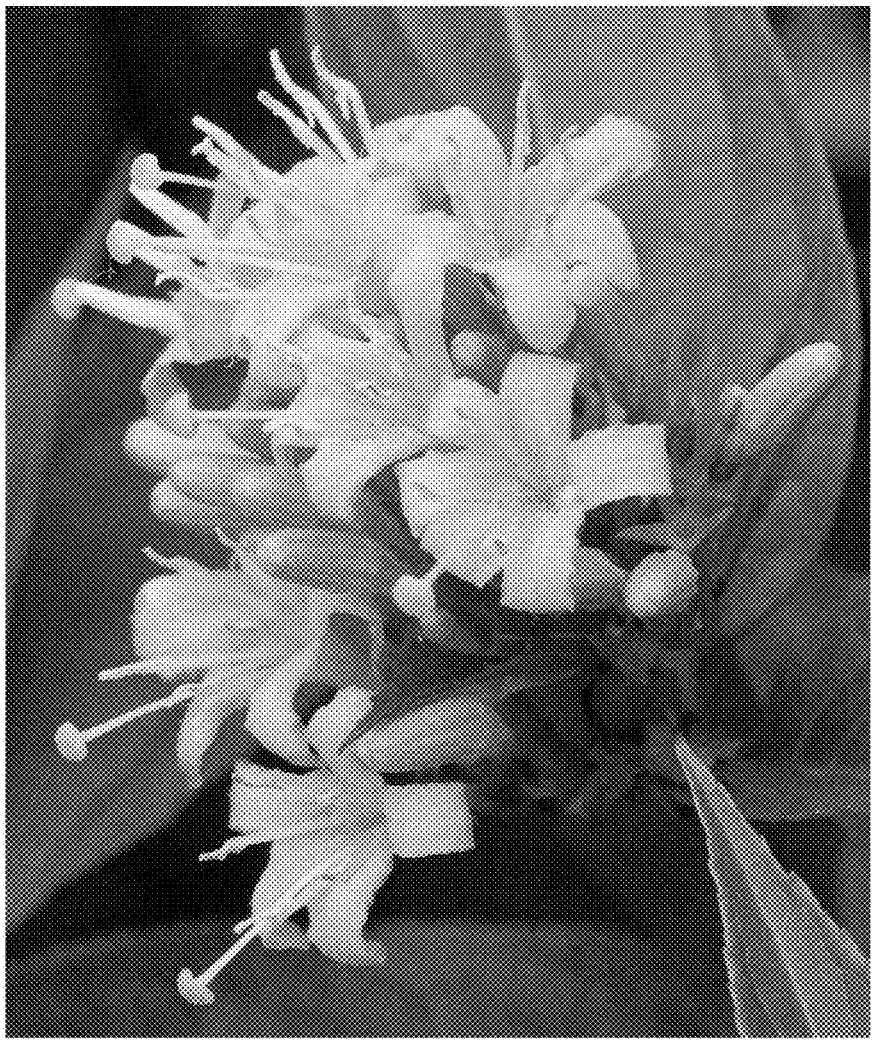

The photograph on the third sheet (FIG. 3) is a close-up view of a typical flowering stem of 'SMNDSA'.

Figure 4:
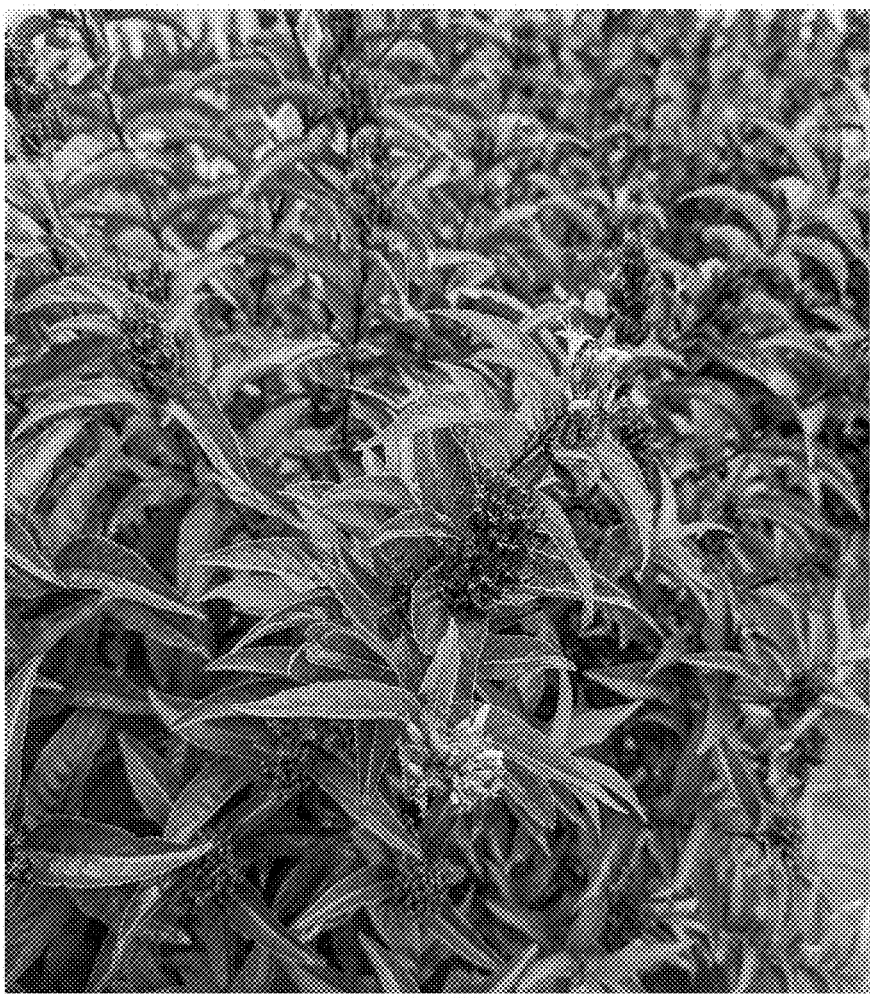

The photograph on the fourth sheet (FIG. 4) is a close-up view of typical fruiting plants of 'SMNDSA'.

Plants used for the aforementioned photographs were grown in an outdoor nursery in Grand Haven, Michigan during late spring and summer and were about two years old.

DETAILED BOTANICAL DESCRIPTION

The following observations, measurements and values describe plants grown in the late spring and early summer in three-gallon containers in a polyethylene-covered greenhouse in Grand Haven, Michigan and under cultural practices typical of commercial *Diervilla* production. During the production of the plants, day temperatures ranged from 18° C. to 27° C. and night temperatures ranged from 5° C. to 10° C. Plants were two years old when the detailed description were taken. In the description, color references are made to The Royal Horticultural Society Colour Chart, 2015 Edition, except where general terms of ordinary dictionary significance are used.

Botanical classification: *Diervilla* x *splendens* 'SMNDSA'.

Parentage:

*Female, or seed, parent.*—*Diervilla* x *splendens* 'Beauregard', not patented.

*Male, or pollen, parent.*—Unknown proprietary selection of *Diervilla* x *splendens*, not patented.

Propagation:

*Type.*—By softwood stem cuttings.

*Time to initiate roots, summer.*—About 10 to 21 days at temperatures ranging from about 18° C. to 27° C.

*Time to produce a rooted young plant, summer.*—About four weeks at temperatures ranging from about 18° C. to 27° C.

*Root description.*—Medium in thickness to thick; fleshy to fibrous; typically white to tan in color, actual color of the roots is dependent on substrate composition, water quality, fertilizer, substrate temperature and physiological age of roots.

*Rooting habit.*—Moderately freely branching; medium density.

Plant description:

*Plant form and growth habit.*—Perennial deciduous shrub; compact, upright to outwardly spreading and uniformly mounding plant habit; vigorous growth habit and rapid growth rate.

*Plant height, soil level to top of foliar plane.*—About 55 cm.

*Plant height, soil level to top of floral plane.*—About 60 cm.

*Plant diameter* (*area of spread*).—About 55 cm.

Lateral branch description:

*Branching habit.*—Freely branching habit; dense and bushy appearance with about 40 lateral branches developing per plant.

*Length.*—About 50 cm.

*Diameter.*—About 4 mm.

*Internode length.*—About 4 cm.

*Aspect.*—Erect to about 30° from vertical.

*Strength.*—Moderately strong.

*Texture and luster.*—Developing, slightly pubescent; developed, smooth, glabrous; longitudinally ridged; matte.

*Color, developing.*—Close to 144B to 144C.

*Color, developed.*—Close to 176A.

Leaf description:

*Arrangement.*—Opposite, simple.

*Length.*—About 9 cm.

*Width.*—About 3 cm.

*Shape.*—Lanceolate.

*Apex.*—Acuminate.

*Base.*—Obtuse.

*Margin.*—Serrulate.

*Texture and luster, upper and lower surfaces.*—Smooth, glabrous; matte.

*Venation pattern.*—Pinnate.

*Color.*—Developing leaves, upper surface: Close to 146A. Developing leaves, lower surface: Close to 146B. Fully expanded leaves, upper surface: Close to 147A; venation, close to 147A. Fully expanded leaves, lower surface: Close to 147B; venation, close to 147B.

*Petioles.*—Length: About 2 mm. Diameter: About 2 mm. Texture and luster, upper and lower surfaces: Smooth, glabrous; matte. Color, upper and lower surfaces: Close 176A.

Flower description:

*Flower appearance and arrangement.*—Salverform flowers arranged in terminal and axillary bipartite cymes; freely flowering habit with about 10 to 20 flowers per inflorescence and about 1,400 flowers developing per plant; flowers face upright to outwardly.

*Fragrance.*—None detected.

*Natural flowering season.*—Plants flower during the summer in Michigan.

*Flower longevity.*—Depending on temperature, individual flowers last about three to five days on the plant; flowers not persistent.

*Flower buds.*—Length: About 5 mm. Diameter: About 2 mm. Shape: Oblong. Texture and luster: Smooth, glabrous; matte. Color: Close to 144B.

*Inflorescence height.*—About 3 cm.

*Inflorescence diameter.*—About 2 cm.

*Flower diameter.*—About 1.5 cm.

*Flower length* (*depth*).—About 1 cm.

*Flower throat diameter.*—About 4 mm.

*Flower tube length.*—About 1 cm.

*Flower tube diameter, proximally.*—About 2 mm.

*Petals.*—Quantity and arrangement: Five fused with apices free and reflexing. Lobe length: About 6 mm. Lobe width: About 2 mm. Lobe shape: Oblong. Lobe apex: Obtuse. Lobe margin: Entire; not undulate. Lobe texture and luster, upper and lower surfaces: Smooth, glabrous; silky; matte. Throat texture and luster: Smooth, glabrous; matte. Tube texture and luster: Smooth, glabrous; matte. Color: When opening and fully opened, upper surface: Close to N144B; throat, close to N144B. When opening and fully opened, lower surface: Close to N144B; tube, close to N144B.

*Sepals*.—Quantity and arrangement: Five in a single whorl fused at the base into a stellate-shaped calyx. Length: About 3 mm. Width: About 1 mm. Shape: Deltoid. Apex: Acute. Margin: Entire. Texture and luster, upper and lower surfaces: Smooth, glabrous; matte. Color: When opening, upper and lower surfaces: Close to 144B. Fully opened, upper and lower surfaces: Close to 144B.

*Peduncles*.—Length: About 1.5 cm. Diameter: About 2 mm. Aspect: About 45° from the stem axis. Strength: Moderately strong. Texture and luster: Smooth, glabrous; matte. Color, upper and lower surfaces: Close to 144B.

*Pedicels*.—Length: About 5 mm. Diameter: About 1 mm. Aspect: About 45° from peduncle axis. Strength: Moderately strong. Texture and luster: Smooth, glabrous; matte. Color, upper and lower surfaces: Close to 144B.

*Reproductive organs*.—Stamens: Quantity per flower: Five. Filament length: About 7 mm. Filament color: Close to N144B. Anther length: About 3 mm. Anther shape: Linear. Anther color: Close to 162B. Pollen amount: Moderate. Pollen color: Close to 162B. Pistils: Quantity per flower: One. Pistil length: About 1.5 cm. Style length: About 1.4 cm. Style color: Close to N144B. Stigma diameter: About 1.5 mm. Stigma shape: Peltate, hemispherical. Stigma color: Close to 144A. Ovary color: Close to 144B. Fruits: Quantity per lateral branch: About 50. Quantity per plant: About 1,000. Length: About 1.5 cm. Diameter: About 5 mm. Shape: Oblong. Color: Close to between 176A and 183A Seeds: Quantity per fruit: About ten. Length: About 1 mm. Diameter: About 1 mm. Color: Close to N199D.

Garden performance: Plants of the new *Diervilla* have been observed to have good garden performance and tolerate rain, wind and to be suitable for USDA Hardiness Zones 3 through 8.

Pathogen & pest resistance: To date, plants of the new *Diervilla* have not been shown to be resistant to pathogens and pests common to *Diervilla* plants.

It is claimed:

1. A new and distinct *Diervilla* plant named 'SMNDSA' as herein illustrated and described.

* * * * *